United States Patent [19]

Usherwood et al.

[11] Patent Number: 5,218,000

[45] Date of Patent: Jun. 8, 1993

[54] THERAPEUTIC POLYAMINE-AMIDES

[75] Inventors: Peter N. R. Usherwood; Barrie W. Bycroft; Ian S. Blagbrough; Alan J. Mather, all of Nottingham, England

[73] Assignee: National Research Development Corporation, England

[21] Appl. No.: 473,983

[22] PCT Filed: Aug. 30, 1989

[86] PCT No.: PCT/GB89/01004

§ 371 Date: Apr. 18, 1990

§ 102(e) Date: Apr. 18, 1990

[87] PCT Pub. No.: WO90/02114

PCT Pub. Date: Mar. 8, 1990

[30] Foreign Application Priority Data

Aug. 30, 1988 [GB] United Kingdom ................ 8820442

[51] Int. Cl.$^5$ ................ A61K 31/165; C07C 233/05; C07C 233/65
[52] U.S. Cl. .................... 514/617; 514/621; 514/622; 564/165; 564/169; 564/170
[58] Field of Search .................... 564/170, 165, 169; 514/617, 622, 620, 621

[56] References Cited

U.S. PATENT DOCUMENTS

| | | | |
|---|---|---|---|
| 3,272,861 | 9/1966 | Riggs | 260/559 |
| 3,390,124 | 6/1968 | Kittridge et al. | 564/170 |
| 4,058,624 | 11/1977 | Jacobus et al. | 424/330 |
| 4,172,094 | 10/1979 | Dybas et al. | 260/570.5 P |
| 4,990,511 | 2/1991 | Nakajima et al. | 514/255 |

FOREIGN PATENT DOCUMENTS

| | | |
|---|---|---|
| 0174085 | 3/1986 | European Pat. Off. |
| 0339927 | 2/1989 | European Pat. Off. |
| 0353753 | 2/1990 | European Pat. Off. |
| 862721 | 3/1961 | United Kingdom |
| 879957 | 10/1961 | United Kingdom |
| 985117 | 3/1965 | United Kingdom |
| 1043345 | 9/1966 | United Kingdom |
| 1122921 | 8/1968 | United Kingdom |

OTHER PUBLICATIONS

Asami et al., Biomedical Research, 10(3), pp. 185-189 (1989).
Martin-Janguy et al., Chem. Abstracts, Abstract 183157, vol. 90 No. 23, Jun. 4, 1979.
B. Meldrum and J. Garthwaite, "Excitatory amino acid neurotoxicity and neurodegenerative disease", Trends in Pharmacological Sciences (TIPS), Special Report 1991 The Pharmacology of Excitatory Amino Acids, pp. 54–62.
J. C. Watkins et al., "Structure–activity relationships in the development of excitatory amino acid receptor agonists and competitive antagonists", Trends in Pharmacological Sciences (TIPS), Special Report 1991, The Pharmacology of Excitatory Amino Acids, p. 4.
Quicke et al., Pesticides Science, 20(4):315–317 (1987).
Oediger, Chem. Abst. 72-21525b (1970).

Primary Examiner—Richard L. Raymond
Assistant Examiner—Shailendra Kumar
Attorney, Agent, or Firm—Rosenman & Colin

[57] ABSTRACT

A compound of formula I optionally in the form of an acid addition salt

I:

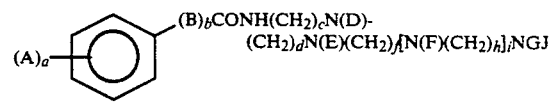

in which formula:
A represents a substituent which is: hydroxyl, O-alkyl, O-cycloalkyl, O-alkenyl, O-aryl, O-aralkyl, O-carbamate, O-carbonate, O-acyl or halogen
a is 0–5;
the substituents A are identical or different when a is more than 1;
B represents a $C_1$–$C_6$ aliphatic hydrocarbon group optionally carrying one or more of the substituents: hydroxyl, amino, halogen, $C_1$–$C_4$ alkoxy, $C_1$–$C_4$ alkyl, aryloxy or carboalkoxy and optionally comprising one or more sites of unsaturation and/or one or more carbonyl groups or ketal derivatives thereof;
b is 0 or 1;
c, d, f and h, which may be identical or different, are 2, 3, 4, 5 or 6; and
i is 0 or 1
D, E and F, which may be identical or different, represent hydrogen or $C_1$–$C_4$ alkyl or cycloalkyl, and
G and J which may be identical or different represent hydrogen, alkyl or cycloalkyl or G and J together with the nitrogen atom to which they are attached represent a saturated heterocyclic ring system.

15 Claims, No Drawings

THERAPEUTIC POLYAMINE-AMIDES

This invention relates to polyamine amides of interest for the treatment of cerebral disorders and in particular psychoses, senile dementia, ischaemia, stroke, hypoxia, aneurysm, epilepsy, Parkinson's disease, Alzheimer's disease, Huntington's chorea, and related syndromes and neurological disorders.

Accordingly, the present invention comprises a compound of formula I optionally in the form of an acid addition salt

I:

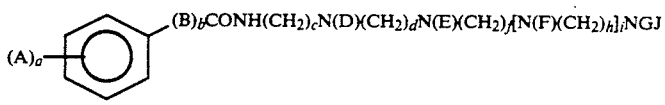

in which formula:
- A represents a substituent which is: hydroxyl, O-alkyl, O-cycloalkyl, O-alkenyl, O-aryl, O-aralkyl, O-carbamate, O-carbonate, O-acyl or halogen
- a is 0–5;
- the substituents A are identical or different when a is more than 1;
- B represents a $C_1$-$C_6$ aliphatic hydrocarbon group optionally carrying one or more of the substituents: hydroxyl, amino, halogen, $C_1$-$C_4$ alkoxy, $C_1$-$C_4$ alkyl, aryloxy or carboalkoxy and optionally comprising one or more sites of unsaturation and/or one or more carbonyl groups or ketal derivatives thereof;
- b is 0 or 1;
- c, d, f and h, which may be identical or different, are 2, 3, 4, 5 or 6; and
- i is 0 or 1
- D, E and F, which may be identical or different, represent hydrogen or $C_1$-$C_4$ alkyl or cycloalkyl, and
- G and J which may be identical or different represent hydrogen, alkyl or cycloalkyl or G and J together with the nitrogen atom to which they are attached represent a saturated heterocyclic ring system.

Typically: when A represents O-alkyl, the alkyl group is $C_1$-$C_4$ alkyl; when A represents O-cycloalkyl the group is cyclohexyl; when A represents O-alkenyl the alkenyl group is a $C_1$-$C_4$ alkenyl group such as ethenyl, propenyl or butenyl; when A represents O-aryl, the aryl group is a phenyl group; when A represents O-aralkyl, the aralkyl group is a $C_7$-$C_{10}$ phenalkyl group; when A represents O-carbamate, the O-carbamate group is of formula $-O-CO-NR^IR^{II}$ wherein $R^I$ and $R^{II}$, which may be identical or different, represent $C_1$-$C_4$ alkyl groups; when A represents O-carbonate, the O-carbonate is of formula $-O-CO-OR^{III}$ wherein $R^{III}$ represents a $C_1$-$C_4$ alkyl group; when A represents O-acyl, the O-acyl group is of formula $-O-CO-R^{IV}$ wherein $R^{IV}$ represents a $C_1$-$C_4$ alkyl group e.g. methyl and when A represents halogen, the halogen is typically Cl, Br or F.

It will be appreciated that the compounds in which A represents a substituent other than hydroxyl or halogen may act through conversion in vivo to the corresponding compound in which the group or groups A are hydroxy groups. Indeed, the present invention extends in general to compounds of formula (I) as defined above in which A is hydroxyl when in pro-drug form.

Although a may be 0–5, it is typically at least 1 and normally no more than 3, mono or di substitution of the aromatic ring being preferred and disposition of a mono substituent e.g. a hydroxyl group, at the 2, 3 or 4 position in the ring being especially so.

The aliphatic hydrocarbon group B is typically unbranched and generally contains no more than two carbon atoms intermediate between the aromatic ring and the carbonyl group of the $CONH(CH_2)_c-$ function. It will be appreciated that, when present, substituents may be identical or different. Sites of unsaturation may be present as double bonds (typically configurationally trans) or triple bonds or both. Groups of the following formula are of particular interest, $R_1$ $R_2$ and $R_3$ representing hydrogen or one or more of the substituents hereinbefore described as carried on the $C_1$-$C_6$ aliphatic hydrocarbon group: $-CHR_1-$, $-CHR_1CHR_2-$, $-CR_1=CR_2-$, $-CHR_1CHR_2CHR_3-$, $-CR_1=CR_2CHR_3-$ and $-CHR_1-CR_2=CR_3-$.

Although $R_1$, $R_2$ and $R_3$ may represent one or more of the hereinbefore identified substituents it is most usual for all to be hydrogen.

Usually no more than one carbonyl group or ketal derivative thereof is present in the group B (i.e. one carbon atom of the $C_{1-6}$ aliphatic hydrocarbon group is substituted by an oxo group or such a group in ketal form) and there is generally at least one other carbon atom present in the carbon chain between the aromatic ring and the $CONH(CH_2)_c-$ function as in the phenylpyruvic and hydroxyphenylpyruvic moieties wherein B represents $-CH_2CO-$, which are of particular interest. When a carbonyl group is derivatised as a ketal group, of formula $-C(OR_a)(OR_b)-$, $R_a$ and $R_b$, which may be identical or different, represent $C_1$-$C_6$ alkyl groups e.g. methyl or ethyl groups or groups which are linked together to form a ring incorporating the carbon and two oxygen atoms as for example in the ethylene ketal wherein $R_a$ and $R_b$ each represent $-CH_2-$.

D, E and F may be $C_{1-4}$ alkyl or, for example, $C_3$-$C_6$ cycloalkyl but it is generally preferred for D, E and F to each represent hydrogen and for i to be zero. In compounds of particular interest the values for c, d and f are each 3 (as in bis (3-aminopropyl)-1,3-propanediamine) or, respectively 3, 4 and 3 (as in spermine).

Although generally the substituents G and J each represent hydrogen, G and J may represent certain organic groups as indicated and particularly each of G and J may independently represent $C_1$-$C_4$ alkyl or $C_3$-$C_6$ cycloalkyl or together may represent a $C_2$-$C_6$ alkylene group, for example a tetramethylene, pentamethylene or hexamethylene group, or a group $-CH_2CH_2-O-CH_2CH_2-$ (to form a morpholine ring system).

Compounds of formula I which are of particular interest include those with the following formulae:

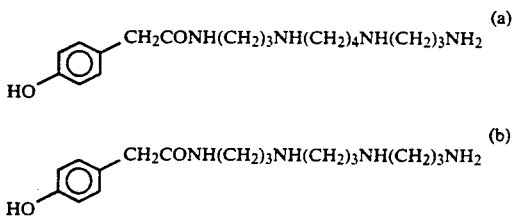

(a) HO-⌬-CH$_2$CONH(CH$_2$)$_3$NH(CH$_2$)$_4$NH(CH$_2$)$_3$NH$_2$ (b) HO-⌬-CH$_2$CONH(CH$_2$)$_3$NH(CH$_2$)$_3$NH(CH$_2$)$_3$NH$_2$

Acid addition salts of compounds of formula (I) in accordance with the invention are preferably pharmaceutically acceptable although other acid addition salts are within the scope of the invention. Suitable salts are those derived from, for example, the following acids: hydrochloric, hydrobromic, sulphuric, nitric, isethionic, phosphoric, maleic, salicylic, p-toluenesulphonic, tartaric, citric, lactobionic, formic, malonic, pantothenic, succinic, naphthalene-2-sulphonic, benzenesulphonic, methanesulphonic and ethanesulphonic. The preferred salts in terms of pharmaceutical acceptability are the ethanesulphonic acid salts.

Such salts may be prepared from the free-base by treatment with the acid suitably in a polar solvent such as water and if necessary with the application of heat.

The compounds of the present invention may be readily produced by reaction between an acid and an amine moiety.

Accordingly to a further aspect of the present invention a process for the production of a compound of formula I comprises reacting an acid of formula II or esterifiable derivative thereof e.g. an acid halide

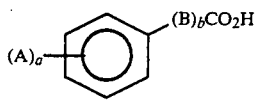

(A)$_a$-⌬-(B)$_b$CO$_2$H    II with an amine or of formula III or acid addition salt thereof:

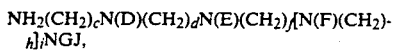

NH$_2$(CH$_2$)$_c$N(D)(CH$_2$)$_d$N(E)(CH$_2$)$_f$[N(F)(CH$_2$)$_h$]$_i$NGJ,    III in which formulae the symbols have the hereinbefore given meanings.

In general the reaction is conducted in an organic solvent such as 1,2-dimethoxyethane or tetrahydrofuran or dioxan in the presence of a coupling reagent such as a carbodiimide e.g. dicyclohexylcarbodiimide or another carbodiimide e.g. 1-cyclohexyl-3-(2-morpholinoethyl)carbodiimide-metho-p-toluenesulphonate (morpho CDI, Aldrich), or 1-(3-dimethylaminopropyl)-3-ethyl-carbodiimide hydrochloride or methiodide (water soluble reagents, EDC, Aldrich), or 1,3-diisopropylcarbodiimide. The product may be readily purified by chromatography and/or lyophilisation.

The acid (or esterifiable derivative) thereof may, for example, be benzoic, phenylacetic, phenylpropanoic, or cinnamic or substituted derivatives e.g. hydroxyphenylglycine, dopa, tyrosine, hydroxyphenylpyruvic-, hydroxyphenylacetic- and hydroxymandelic acid.

The present invention further includes within its scope a composition for the treatment of psychoses, senile dementia, ischaemia, stroke, hypoxia, aneurysm, epilepsy, Parkinson's disease, Alzheimer's disease, Huntington's chorea, and related syndromes and neurological disorders which comprises a compound of formula I together with a pharmaceutically acceptable diluent or carrier.

The compounds of the present invention may be formulated by standard or novel techniques to give, if desired, unit dosage forms. Although the dosage for a particular clinical application must be ascertained by trial, for general guidance appropriate intravenous dosages usually lie in the range 5-500 μg/kg but exceptionally above this i.e. up to 1 mg/kg or, rarely, up to 5 mg/kg. Oral dosages usually lie in the range 1-100 mg/kg.

The present invention also includes within its scope a method of treating a patient suffering from a psychotic disorder, senile dementia, ischaemia, stroke, hypoxia, aneurysm, epilepsy, Parkinson's disease, Alzheimer's disease, Huntington's chorea or a related syndrome or neurological disorder, in which the patient is administered an amount of a compound of formula I effective to reduce, remove or prevent symptoms of the disorder.

The compound may be administered orally, parenterally (including subcutaneously, intramuscularly and intravenously). The administration will generally be carried out repetitively at intervals, for example once or several times a day.

The amount of compounds of formula (I), as hereinbefore defined in accordance with the invention, which is required in order to be effective for treating mammals will, of course, vary and is ultimately at the discretion of the medical or veterinary practitioner treating the mammal in each particular case. The factors to be considered by such a practitioner, e.g. a physician, include the route of administration and pharmaceutical formulation; the mammal's body weight, surface area, age and general condition; and the particular salt to be administered.

The present invention further includes within its scope a compound of formula I hereinbefore described for use in therapy.

The invention is illustrated by the following Examples:

GENERAL PROCEDURE FOR THE PREPARATION OF MONOACYL SPERMINES

To a solution of the required carboxylic acid in an organic solvent such as 1,2-dimethoxyethane or dichloromethane an activating agent e.g. dicyclohexyl carbodiimide was added. The polyamine was introduced in slight excess (two-four fold) in order to increase the yield of the desired monoacylated product. The product was isolated by chromatography over Kieselgel 60 (230-400 mesh). The final product was always soluble in water and was therefore purified by lyophilisation as a final step.

Locust Test Method and Rationale

The compounds were assayed for biological activity on the isolated, retractor unguis nerve-muscle preparation of the locust *Schistocerca gregaria* (Usherwood, P.N.R and Machili, P. (1968) J. Exp. Biol., 49: 341.). Isolated muscle preparations were bathed continuously in standard locust saline in a bath of volume 250 μl. Twitch tension recordings of the muscle were made to electrical stimulation of its motor innervation supramaximal voltage, frequency 0.1 Hz).

The locust isolated retractor unguis nerve-muscle is a preparation with well characterised muscle receptors belonging to the quisqualate-sensitive class (Boden, P.

et al., (1986) Brain Res., 385: 205.). This preparation has previously been employed to identify antogonists of excitatory amino acid receptors, (e.g. Bateman, A. et al., (1985) Brain Res., 339: 237 and Budd, T. et al., (1988) Brain Res., 448: 30.). Excitatory amino acid receptors are also believed to be of considerable importance in the mammal and for therapeutic applications.

EXAMPLE 1

N-(2-Hydroxyphenylacetyl)-spermine

To a solution of 2-hydroxyphenylacetic acid (50 mg, 0.33 mMol) in 1,2-dimethoxyethane (DME) (1 ml) was added a solution of dicyclohexyl carbodiimide (71 mg, 0.34 mMol, 1.05 equivalents) in DME (1 ml) in one portion of 25° C. The colourless mixture was allowed to stand at 25° C. for 3 h during which time a voluminous white precipitate of the urea was formed. This precipitate was then removed by filtration and the residue washed with DME (2×1 ml). The filtrate and the washings were combined and a solution of spermine (351 mg, 1.73 mMol, 5.3 equivalents) in DME/dimethylformamide (2 ml, 1:1) was added in one portion. The colourless, homogeneous solution was sealed under an atmosphere of nitrogen and allowed to stand at 25° C. for 48 h. The solution was concentrated in vacuo (water aspirator) and then the residue was applied to a column of silica gel (Kieselgel 60, 230–400 mesh). The product was eluted with dichloromethane/methanol/0.880 ammonia solution (4:2:1). The desired amide was eluted in fractions 9–14 (10 ml fractions) and was homogeneous when monitored by tlc on silica ($CH_2Cl_2$/MeOH/$NH_4OH$, 4:2:1), $R_f=0.25$, chromatogram visualised by inspection under UV light (254 nm) and by the production of a pink-purple stain with 0.3% ninhydrin in solution in acidic alcohol. The fractions containing the product were combined and concentrated in vacuo to yield a colourless oil. This oil was dissolved in methanol (2 ml), filtered and the solution was then concentrated in vacuo (51 mg, 46%). The residue was dissolved in distilled water (2 ml) and lyophilised which gave the amide as a colourless, viscous oil (48 mg) whose spectroscopic data include: $UV_{max}$ 271 ($e_{max}$1 000) and 289 sh nm; pmr (90 MHz, $^2H_2O$) 1.5–1.9 (m, 8H, 4×$CH_2$—$CH_2$), 2.6–2.9 (m, 10H, 5×$CH_2$—N), 3.25 (t, J=7, 2H, $CON^2H$—$CH_2$—$CH_2$, 3.55 (s, 2H, Ar—$CH_2$—CO), 6.55–6.85 (m, $\overline{2H}$, 2×ArH 3,5), and 7.1–7.3 (m, 2H, 2×Ar$\overline{H}$ 4,6)ppm; M+1 337 ($\overline{FAB}$ matrix m-nitrobenzyl alcohol) $C_{18}H_{32}N_4O_2$ requires M+336).

The potency of this monoacylated spermine as an antagonist of the complex formed by the invertebrate L-quisqualate sub-type L-glutamate receptor and its ion channel was assayed using the electrically stimulated retractor unguis muscle of the locust (*Schistocerca gregaria*). Twitch amplitude was reduced (1% inhibition) from control (100%) levels at the following concentrations:

| | |
|---|---|
| 3 × $10^{-8}$ M | 10% inhibition of twitch |
| 3 × $10^{-7}$ M | 15% |
| 3 × $10^{-6}$ M | 20% |
| 1.5 × $10^{-5}$ M | 30% |
| 3 × $10^{-5}$ M | 30% |
| 1.5 × $10^{-4}$ M | 85% |
| 3 × $10^{-4}$ M | 90% |
| The $IC_{50}$ = 6.2 × $10^{-5}$ M | |

EXAMPLE 2

N-(3-Hydroxyphenylacetyl)-spermine

To a solution of 3-hydroxyphenylacetic acid (50 mg, 0.33 mMol) in 1,2-dimethoxyethane (DME) (1 ml) was added a solution of dicyclohexyl carbodiimide (75 mg, 0.36 mMol, 1.1 equivalents) in DME (1 ml) in one portion of 25° C. The colourless mixture was allowed to stand at 25° C. for 3 h during which time a voluminous white precipitate of the urea was formed. This precipitate was then removed by filtration and the residue washed with DME (2×1 ml). The filtrate and the washings were combined and a solution of spermine (167 mg, 0.83 mMol, 2.5 equivalents) in DME/dimethylformamide (2 ml, 1:1) was added in one portion. The colourless, homogeneous solution was sealed under an atmosphere of nitrogen and allowed to stand at 25° C. for 24 h. The solution was concentrated in vacuo (water aspirator) and then the residue was applied to a column of silica gel (Kieselgel 60, 230–400 mesh). The product was eluted with dichloromethane/methanol/0.880 ammonia solution (4:2:1). The desired amide was eluted in fractions 12–18 (10 ml fractions) and was homogeneous when monitored by tlc on silica ($CH_2Cl_2$/MeOH/$NH_4OH$, 4:2:1), $R_f=0.18$, chromatogram visualised by inspection under UV light (254 nm) and by the production of a pink-purple stain with 0.3% ninhydrin in solution in acidic alcohol. The fractions containing the product were combined and concentrated in vacuo to yield a colourless oil. This oil was dissolved in methanol (2 ml), filtered and the solution was then concentrated in vacuo (36 mg, 33%). The residue was dissolved in distilled water (2 ml) and lyophilised which gave the amide as a colourless, viscous oil (30 mg) whose spectroscopic data include: $UV_{max}$ 274 sh, 278 ($e_{max}$ 950), and 290 sh nm; pmr (90 MHz, $^2H_2O$) 1.2–2.0 (m, 8H, 4×$CH_2$—$CH_2$), 2.5–2.9 (m, 10H, 5×$CH_2$—N), 3.3 (t, J=7, 2H, $CON^2H$—$CH_2$—$CH_2$), 3.5 (s, 2H, Ar—$CH_2$—CO), 6.45–6.75 (m, $\overline{3H}$, 3×Ar$\overline{H}$ 2,4,6), and 7.0–7.3 (m, 1H, Ar$\overline{H}$ 5)ppm: M+1 337 ($\overline{FAB}$ matrix m-nitrobenzyl alcohol) ($C_{18}H_{32}N_4O_2$ requires M+336).

The potency of this monoacylated spermine as an antagonist of the complex formed by the invertebrate L-quisqualate sub-type L-glutamate receptor and its ion channel was assayed using the electrically stimulated retractor unguis muscle of the locust (Schistocerca gregaria). Twitch amplitude was reduced from control (100%) levels at the following concentrations:

| | |
|---|---|
| 3 × $10^{-8}$ M | 30% |
| 3 × $10^{-7}$ M | 35% |

EXAMPLE 3

N-(4-Hydroxyphenylacetyl)-spermine

To a solution of 4-hydroxyphenylacetic acid (80 mg, 0.53 mMol) in 1,2-dimethoxyethane (DME) (1 ml) was added a solution of dicyclohexyl carbodiimide (120 mg, 0.58 mMol, 1.1 equivalents) in DME (1 ml) in one portion at 25° C. The colourless mixture was allowed to stand at 25° C. for 3 h during which time a voluminous white precipitate of the urea was formed. This precipitate was then removed by filtration and the residue washed with DME (2×1 ml). The filtrate and the washings were combined and a solution of spermine (600 mg, 2.97 mMol, 5.6 equivalents) in DME/dimethylformamide (2 ml, 1:1) was added in one portion. The colourless, homogeneous solution was sealed under an atmosphere of nitrogen and allowed to stand at 25° C. for 48 h. The solution was concentrated in vacuo (water spirator) and then the residue was applied to a column of silica gel (Kieselgel 60, 230–400 mesh). The product was eluted with dichloromethane/methanol/0.880 ammonia solution (4:2:1). The desired amide was eluted in fractions 8–13 (10 ml fractions) and was homogeneous when monitored by tlc on silica (CH$_2$Cl$_2$/MeOH/N-H$_4$OH, 4:2:1), R$_f$=0.17, chromatogram visualised by inspection under UV light (254 nm) and by the production of a pink-purple stain with 0.3% ninhydrin in solution in acidic alcohol. The fractions containing the product were combined and concentrated in vacuo to yield a colourless oil. This oil was dissolved in methanol (2 ml), filtered and the solution was then concentrated in vacuo (65 mg, 37%). The residue was dissolved in distilled water (2 ml) and lyophilised which gave the amide as a colourless, viscous oil (57 mg) whose spectroscopic data include: UV$_{max}$ 220 (e$_{max}$ 6 000) and 270 (e$_{max}$ 1 300) nm: pmr (90 MHz, $^2$H$_2$O) 1.2–2.0 (m, 8H, 4×CH$_2$—CH$_2$—CH$_2$), 2.5–2.9 (m, 10H, 5×CH$_2$—N), 3.2 (t, J=7, 2H, CON$^2$H—CH$_2$—CH$_2$), 3.4 (s, 2H, Ar—CH$_2$—CO), 6.7 (d, J=8, 2H, 2×ArH 3,5), and 7.1 (d, J=8, 2H, 2×ArH 2,6)ppm: M+1 337 (FAB matrix m-nitrobenzyl alcohol) (C$_{18}$H$_{32}$N$_4$O$_2$ requires M+336).

The potency of this monoacylated spermine as an antagonist of the complex formed by the invertebrate L-quisqualate sub-type L-glutamate receptor and its ion channel was assayed using the electrically stimulated retractor unguis muscle of the locust (Schistocerca gregaria). Twitch amplitude was reduced from control (100%) levels at the following concentrations:

| | |
|---|---|
| 5.9 × 10$^{-7}$ M | 9% |
| 5.9 × 10$^{-6}$ M | 25% |
| 2.95 × 10$^{-5}$ M | 74% |
| 4.43 × 10$^{-5}$ M | 91% |
| 5.9 × 10$^{-5}$ M | 96% |
| The IC$_{50}$ = 8.7 × 10$^{-6}$ M | |

EXAMPLE 4

N-(2-Hydroxyphenylpropanoyl)-spermine

To a solution of 2-hydroxyphenylpropanoic acid (61 mg, 0.37 mMol) in 1,2-dimethoxyethane (DME) (1 ml) was added a solution of dicyclohexylcarbodiimide (76 mg, 0.37 mMol) in DME (1 ml) in one portion at 25° C. The colourless mixture was allowed to stand at 25° C. for 3 h during which time a voluminous white precipitate of the urea was formed. This precipitate was then removed by filtration and the residue washed with DME (2×1 ml). The filtrate and the washings were combined and a solution of spermine (300 mg, 1.48 mMol, 4.0 equivalents) in DME/dimethylformamide (2 ml, 1:1) was added in one portion. The colourless, homogeneous solution was sealed under an atmosphere of nitrogen and allowed to stand at 25° C. for 48 h. The solution was concentrated in vacuo (water aspirator) and the residue was then applied to a column of silica gel (Kieselgel 60, 230–400 mesh). The product was eluted with dichloromethane/methanol/0.880 ammonia solution (4:2:1). The desired amide was eluted in fractions 7–11 (10 ml fractions) and was homogeneous when monitored by tlc on silica (CH$_2$Cl$_2$/MeOH/NH$_4$OH, 4:2:1), R$_f$=0.33, chromatogram visualised by inspection under UV light (254 nm) and by the production of a pink-purple stain with 0.3% ninhydrin in solution in acidic alcohol. The fractions containing the product were combined and concentrated in vacuo to yield a colourless oil.

This oil was dissolved in methanol (2 ml), filtered and the solution was then concentrated in vacuo (112 mg, 87%). The residue was dissolved in distilled water (2 ml) and lyophilised which gave the amide as a colourless, viscous oil (82 mg) whose spectroscopic data include: pmr (90 MHz, $^2$H$_2$O) 1.3–2.1 (m, 8H, 4×CH$_2$—CH$_2$), 2.5–3.1 (m, 14H, 5×CH$_2$—N and Ar—CH$_2$—CH$_2$), 3.3 (t, J=7, 2H, CON$^2$H—CH$_2$—CH$_2$), 6.7–7.0 (m, 2H, 2×ArH 3,5), and 7.1–7.4 (m, 2H, 2×ArH 4,6)ppm.

The potency of this monoacylated spermine as an antagonist of the complex formed by the invertebrate L-quisqualate sub-type L-glutamate receptor and its ion channel was assayed using the electrcically stimulated retractor unguis muscle of the locust (Schistocerca gregaria). Twitch amplitude was reduced from control levels between the following concentrations: 1×10$^{-5}$M and 9×10$^{-5}$M, such that an approximately 50% reduction was obtained at 5×10$^{-5}$M.

EXAMPLE 5

N-(3-Hydroxyphenylpropanoyl)-spermine

To a solution of 3-hydroxyphenylpropanoic acid (167 mg, 1.01 mMol) in dichloromethane (5 ml) was added dicyclohexylcarbodiimide (226 mg, 1.10 mMol, 1.1 equivalents) in one portion at 25° C. The colourless mixture was allowed to stand at 25° C. for 2 h during which time a voluminous white precipitate of the urea was formed. This precipitate was then removed by filtration and the residue washed with dichloromethane (1 ml). The filtrate and the washings were combined and spermine (400 mg, 1.98 mMol, 1.96 equivalents) was added in one portion. The colourless, homogeneous solution was sealed under an atmosphere of nitrogen and allowed to stand at 25° C. for 4 h. The solution was concentrated in vacuo (water aspirator) and the residue was then applied to a column of silica gel (Kieselgel 60, 230–400 mesh). The product was eluted with dichloromethane/methanol/0.880 ammonia solution (4:2:1). The desired amide was eluted in fractions 13–19 (10 ml fractions) and was homogeneous when monitored by tlc on silica (CH$_2$Cl$_2$/MeOH/NH$_4$OH, 4:2:1), R$_f$=0.11, chromatogram visualised by inspection under UV light (254 nm) and by the production of a pink-purple stain with 0.3% ninhydrin in solution in acidic alcohol. The fractions containing the product were combined and concentrated in vacuo to yield a colourless oil. This oil was dissolved in methanol (2 ml), filtered and the solution was then concentrated in vacuo (105 mg, 30%). The residue was dissolved in distilled water (2 ml) and lyophilised which gave the amide as a colourless glass (80 mg) whose spectroscopic data include: UV$_{max}$ 217 (e$_{max}$ 2 500) and 272 (e$_{max}$ 1 200)nm; pmr (90 MHz, $^2$H$_2$O) 1.5–2.0 (m, 8H, 4×CH$_2$—CH$_2$), 2.4–3.0 (m, 14H, 5×CH$_2$—N and Ar—CH$_2$—CH$_2$), 3.2 (t, J=7, 2H, CON$^2$H—CH$_2$—CH$_2$), 6.55–6.75 (m, 3H, 3×ArH 2,4,6), and 7.05–7.3 (m, H, ArH 5)ppm; M+1 351 (FAB matrix m-nitrobenzyl alcohol) C$_{19}$H$_{34}$N$_4$O$_2$ requires M+ 350).

The potency of this monoacylated spermine as an antagonist of the complex formed by the invertebrate L-quisqualate sub-type L-glutamate receptor and its ion channel was assayed using the electrically stimulated retractor unguis muscle of the locust (*Schisocerca gregaria*). Twich amplitude was reduced from control (100%) levels at the following concentrations:

| | |
|---|---|
| $1.08 \times 10^{-7}$ M | 10% inhibition of twitch |
| $1.08 \times 10^{-6}$ M | 15% |

EXAMPLE 6

N-(4-Hydroxycinnamoyl)-spermine

To a solution of 4-hydroxycinnamic acid (82 mg, 0.50 mMol) in 1,2-dimethoxyethane (DME) (1 ml) was added a solution of dicyclohexylcarbodiimide (106 mg, 0.51 mMol, 1.03 equivalents) in DME (1 ml) in one portion at 25° C. The colourless mixture was allowed to stand at 25° C. for 3 h during which time a voluminous white precipitate of the urea was formed. This precipitate was then removed by filtration and the residue washed with DME (2×1 ml). The filtrate and the washings were combined and a solution of spermine (336 mg, 1.66 mMol, 3.3 equivalents) in DME/dimethylformamide (2 ml, 1:1) was added in one portion. The yellow, homogeneous solution was sealed under an atmosphere of nitrogen and allowed to stand at 25° C. for 48 h. The solution was concentrated in vacuo (water aspirator) and the residue was then applied to a column of silica gel (Kieselgel 60, 230–400 mesh). The product was eluted with dichloromethane/methanol/0.880 ammonia solution (4:2:1). The desired amide was eluted in fractions 11–16 (10 ml fractions) and was homogeneous when monitored by tlc on silica ($CH_2Cl_2$/MeOH/$N$-$H_4OH$, 4:2:1), $R_f=0.21$, chromatogram visualised by inspection under UV light (254 nm) and by the production of a pink-purple stain with 0.3% ninhydrin in solution in acidic alcohol. The fractions containing the product were combined and concentrated in vacuo to yield a pale yellow oil.

This oil was dissolved in methanol (2 ml), filtered and the solution was then concentrated in vacuo (30 mg, 17%). The residue was dissolved in distilled water (2 ml) and lyophilised which gave the amide as a colourless, viscous oil (30 mg) whose spectroscopic data include: $UV_{max}$ 224 293 and 312 sh nm; pmr (90 MHz, $^2H_2O$) 1.4–2.0 (m, 8H, 4×$CH_2$—$CH_2$), 2.6–3.0 (m, 10H, 5×$CH_2$—N), 3.35 (t, J=7, $\overline{2H}$, $CON^2H$—$CH_2$—$CH_2$), 6.36 $\overline{(d}$, J=16, 1H, CH=CH—CO) 6.6–6.$\overline{9}$ (m, 2H, 2×ArH 3,5), and 7.2–7.6 ($\overline{m}$, 3H, 2×Ar$\overline{H}$ 2,6 and Ar—$\overline{CH}$=CH)ppm; M+1 349 (FAB matrix m-nitrobenzyl alcohol) $C_{19}H_{32}N_4O_2$ requires M+ 348).

The potency of this monoacylated spermine as an antagonist of the complex formed by the invertebrate L-quisqualate sub-type L-glutamate receptor and its ion channel was assayed using the electrically stimulated retractor unguis muscle of the locust (Schistocerca gregaria). Twitch amplitude was reduced from control (100%) levels at the following concentrations:

| | |
|---|---|
| $10^{-10}$ M | 4% |
| $10^{-9}$ M | 18% |
| $10^{-8}$ M | 24% |
| $10^{-7}$ M | 33% |
| $10^{-6}$ M | 56% |
| $10^{-5}$ M | 70% |
| The $IC_{50}$ = $6 \times 10^{-5}$ M | |

EXAMPLE 7

N-(2,4-Dihydroxyphenylacetyl)-spermine

To a solution of 2,4-dibenzyloxyphenylacetic acid N-hydroxysuccinimide ester (93 mg, 0.22 mMol) in dichloromethane (3 ml) was added spermine (112 mg, 0.55 mMol, 2.5 equivalents)) in one portion. The colourless, homogeneous solution was sealed under an atmosphere of nitrogen and allowed to stand at 25° C. for 24 h. The solution was concentrated in vacuo (water aspirator) and the residue was then applied to a column of silica gel (Kieselgel 60, 230–400 mesh). The product was eluted with dichloromethane/methanol/-0.880 ammonia solution (8:4:1). The desired amide was eluted in fractions 10–15 (10 ml fractions) and was homogeneous when monitored by tlc on silica ($CH_2Cl_2$/MeOH/$N$-$H_4OH$, 4:2:1), $R_f=0.22$, chromatogram visualised by inspection under UV light (254 nm) and by the production of a pink-purple stain with 0.3% ninhydrin in solution in acidic alcohol. The fractions containing the product were combined and concentrated in vacuo to yield a pale yellow gum.

This gum was dissolved in methanol (2 ml), filtered and the solution was then concentrated in vacuo (50 mg, 45%). The residue was dissolved in distilled water (2 ml) and lyophilised which gave the amide as a white solid (43 mg). The amide was dissolved in water (2 ml) and aqueous hydrochloric acid (2M, 0.5 ml) and palladium on carbon (10%, 11 mg) were then added. The mixture was stirred and hydrogenated at 1 atm and 25° C. for 24 h. The catalyst was removed by filtration through a pad of Kieselguhr, eluted with water. The clear solution was then lyophilised which gave the desired amide trihydrochloride (34 mg) as a colourless glass whose spectroscopic data include: $UV_{max}$ 293 ($e_{max}$ 1 500)nm at pH=11; M+1 353 (FAB matrix m-nitrobenzyl alcohol) $C_{18}H_{32}N_4O_3$ requires M+ 352).

The potency of this monoacylated spermine as an antagonist of the complex formed by the invertebrate L-quisqualate sub-type L-glutamate receptor and its ion channel was assayed using electrically stimulated the retractor unguis muscle of the locust (*Schistocerca gregaria*). Twitch amplitude was reduced from control levels between the following concentrations: $1\times10^{-5}$M and $9\times10^{-5}$M, such that an approximately 50% reduction was obtained at $5\times10^{-5}$M.

EXAMPLE 8

N-(3,4-Dihydroxyphenylacetyl)-spermine

To a solution of 3,4-dibenzyloxyphenylacetic acid N-hydroxysuccinimide ester (115 mg, 0.26 mMol) in dichloromethane (5 ml) was added spermine (128 mg, 0.63 mMol, 2.45 equivalents) in one portion. The colourless, homogeneous solution was sealed under an atmosphere of nitrogen and allowed to stand at 25° C. for 22 h. The solution was concentrated in vacuo (water aspirator) and the residue was then applied to a column of silica gel (Kieselgel 60, 230–400 mesh). The product was eluted with dichloromethane/methanol/0.880 ammonia solution (8:4:1). The desired amide was eluted in fractions 18–26 (10 ml fractions) and was homogeneous when monitored by tlc on silica ($CH_2Cl_2$/MeOH/$N$-$H_4OH$, 8:4:1), $R_f=0.16$, chromatogram visualised by inspection under UV light (254 nm) and by the production of a pink-purple stain with 0.3% ninhydrin in solution in acidic alcohol. The fractions containing the product were combined and concentrated in vacuo to yield a pale yellow gum.

This gum was dissolved in methanol (2 ml), filtered and the solution was then concentrated in vacuo (48 mg, 35%). The residue was dissolved in distilled water (2 ml) and lyophilised which gave the amide as a colourless, viscous oil (46 mg). The amide was dissolved in water (2 ml) and aqueous hydrochloric acid (2M, 0.5 ml) and palladium on carbon (10%, 12 mg) were then added. The mixture was stirred and hydrogenated at 1 atm and 25° C. for 24 h. The catalyst was removed by filtration through a pad of Kieselguhr, eluted with water. The clear solution was then lyophilised which gave the desired amide trihydrochloride as a colourless glass (32 mg) whose spectroscopic data include: $UV_{max}$ 2 700) and 291 ($e_{max}$ 2 500)nm at pH=11.

The potency of this monoacylated spermine as a non-competitive antagonist of the complex formed by the invertebrate L-quisqualate sub-type L-glutamate receptor and its ion channel was assayed using the electrically stimulated retractor unguis muscle of the locust (*Schistocerca gregaria*). Twitch amplitude was reduced from control levels between the following concentrations: $1 \times 10^{-4}$M and $9 \times 10^{-4}$M, such that an approximately 50% reduction was obtained at $5 \times 10^{-4}$M.

EXAMPLE 9

N-(3,5-Dihydroxyphenylacetyl)-spermine

To a solution of 3,5-dibenzyloxyphenylacetic acid (86 mg, 0.247 mMol) in dichloromethane (1 ml) was added a solution of dicyclohexylcarbodiimide (55 mg, 0.27 mMol 1.08 equivalents) in dichloromethane (1 ml) in one portion at 25° C. The colourless mixture was allowed to stand at 25° C. for 1.5 h during which time a voluminous white precipitate of the urea was formed. This precipitate was then removed by filtration and the residue washed with dichloromethane (2×1 ml). The filtrate and the washings were combined and a solution of spermine (150 mg, 0.74 mMol, 3.0 equivalents) in dichloromethane (1 ml) was added in one portion. The colourless, homogeneous solution was sealed under an atmosphere of nitrogen and allowed to stand at 25° C. for 4 h. The solution was concentrated in vacuo (water aspirator) and the residue was then applied to a column of silica gel (Kieselgel 60, 230–400 mesh). The product was eluted with dichloromethane/methanol/0.800 ammonia solution (8:4:1). The desired amide was eluted in fractions 15–18 (10 ml fractions) and was homogeneous when monitored by tlc on silica ($CH_2Cl_2$/MeOH/NH$_4$OH, 4:2:1) $R_f$=0.11, chromatogram visualised by inspection under UV light (254 nm) and by the production of a pink-purple stain with 0.3% ninhydrin in solution in acidic alcohol. The fractions containing the product were combined and concentrated in vacuo to yield a pale yellow gum.

This gum was dissolved in methanol (2 ml), filtered and the solution was then concentrated in vacuo (29 mg, 22%). The residue was dissolved in distilled water (2 ml) and lyophilised which gave the amide as a pale yellow solid (29 mg). The amide was dissolved in water (2 ml) and aqueous hydrochloric acid (2M, 0.5 ml) and palladium on carbon (10%, 11 mg) were then added. The mixture was stirred and hydrogenated at 1 atm and 25° C. for 22 h. The catalyst was removed by filtration through a pad of kieselguhr, eluted with water. The clear solution was then lyophilised which gave the desired amide trihydrochloride (24 mg) as a colourless glass whose spectroscopic data include:$UV_{max}$ 290 ($e_{max}$ 1 300) nm at pH=11; M+1 353 (FAB matrix m-nitrobenzyl alcohol) $C_{18}H_{32}N_4O_3$ requires M+ 352).

The potency of this monoacylated spermine as an antagonist of the complex formed by the invertebrate L-quisqualate sub-type L-glutamate receptor and its ion channel was assayed using the electrically stimulated retractor unguis muscle of the locust (*Schistocerca gregaria*). Twitch amplitude was reduced from control levels between the following concentrations:

| | |
|---|---|
| $1.07 \times 10^{-6}$ M | 25% |
| $1.07 \times 10^{-5}$ M | 45% |

EXAMPLES 10–21

In the present Examples, compounds of formula I were prepared by following the above General Procedure and adapting the methods described in Examples 1 to 7. The compounds prepared together with an indication of their potency as L-glutamate antagonists when tested in the locust leg retractor muscle pharmacological screen follow:

EXAMPLE 10

N-2-Hydroxybenzoyl)-spermine

According to the General Procedure using 2-hydroxybenzoic acid (138 mg, 1.00 mMol). dicyclohexylcarbodiimide (226 mg, 1.10 mMol), and spermine (400 mg, 1.98 mMol) in dichloromethane (6 ml), activation during 3 h and coupling over 4 h. The product was eluted over silica gel with dichloromethane/methanol/0.880 ammonia solution (4:2:1). The desired amide was in fractions 8–15 and was homogeneous when monitored by tlc on silica ($CH_2Cl_2$/MeOH/NH$_4$OH, 4:2:1), $R_f$=0.23, (98 mg, 29%), lyophilisation gave 64 mg of a colorless, viscous oil whose spectroscopic data include:pmr (90 MHz, $^2H_2O$) 1.5–1.9 (m, 8H, 4×$CH_2$—$CH_2$, 2.6–2.9 (m, 10H, 5×$CH_2$—N), 3.25 (t, J=7, 2H, $CON^2H$—$CH_2$—$CH_2$, 6.55–6.85 (m, 2H, 2×Ar$\underline{H}$ 3,5), and 7.1–7.3 (m, 2H, 2×Ar$\underline{H}$ 4,6) ppm; M+1 323 (FAB matrix m-nitrobenzyl alcohol and sodium chloride) $C_{17}H_{30}N_4O_2$ requires M+ 322).

The potency of this monoacylated spermine as an antagonist of the invertebrate L-quisqualate sub-type L-glutamate receptor and its ion channel was assayed using the electrically stimulated retractor unguis muscle of the locust (*Schistocerca gregaria*). Twitch amplitude was reduced from control level at $1.09 \times 10^{-5}$M by approximately 25%.

EXAMPLE 11

N-(3-Hydroxybenzoyl)-spermine

According to the General Procedure using 3-Hydroxybenzoic acid (138 mg, 1.00 mMol), dicyclohexylcarbodiimide (226 mg, 1.10 mMol), and spermine (400 mg, 1.98 mMol) in dichloromethane (6 ml), activation during 3 h and coupling over 17 h. The product was eluted over silica gel with dichloromethane/methanol/0.880 ammonia solution (4:2:1). The desired amide was in fractions 8–13 was homogeneous when monitored by tlc on silica ($CH_2Cl_2$/MeOH/NH$_4$OH, 4:2:1), $R_f$=0.29, (76 mg, 24%), lyophilisation gave 52 mg of a colorless, viscous oil whose spectroscopic data include:pmr (90 MHz, $^2H_2O$) 1.4–1.9 (m, 8H, 4×$CH_2$—$CH_2$), 2.5–2.9 (m, 10H, 5×$CH_2$—N), 3.25 (t, J=7, 2H, $CON^2H$—$CH_2$—$CH_2$), 6.5–6.8 (m, 3H, 3×ArH 2,4,6), and 7.0–7.3 (m, 1H, ArH 5) ppm; M+1 323 (FAB matrix m-nitrobenzyl alcohol and sodium chloride) $C_{17}H_{30}N_4O_2$ requires M+ 322).

The potency of this monoacylated spermine as an antagonist invertebrate L-quisqualate sub-type L-glutamate receptor and its ion channel was assayed using the electrically stimulated retractor unguis muscle of the locust (Schistocerca gregaria). Twitch amplitude was reduced from control levels at $1.02 \times 10^{-5}M$ by approximately 40%.

EXAMPLE 12

N-(4-Hydroxybenzoyl)-spermine

According to the General Procedure using 4-hydroxybenzoic acid (80 mg, 0.58 mMol), dicyclohexylcarbodiimide (125 mg, 0.61 mMol), and spermine (430 mg, 2.13 mMol) in DME/DMF (4 ml, 3:1), activation during 3 h and coupling over 48 h. The product was eluted over silica gel with dichloromethane/methanol/0.880 ammonia solution (2:2:1). The desired amide was in fractions 8–12 and was homogeneous when monitored by tlc on silica ($CH_2Cl_2/MeOH/NH_4OH$, 2:2:1), $R_f=0.29$, (23 mg, 12%), lyophilisation gave 7 mg of a colourless, viscous oil whose spectroscopic data include: pmr (90 MHz, $^2H_2O$) 1.4–1.9 (m, 8H, $4 \times CH_2-CH_2$), 2.5–2.9 (m, 10H, $5 \times CH_2-N$), 3.25 (t, J=7, 2H, $CON^2H-CH_2-CH_2$) 6.6–6.9 (m, 2H, 2×ArH 3,5), and 7.0–7.3 (m, 2H, 2×ArH2,6)ppm; M+1 323 (FAB matrix m-nitrobenzyl alcohol) $C_{17}H_{30}N_4O_2$ requires M+ 322).

The potency of this monoacylated spermine as an antagonist of the invertebrate L-quisqualate sub-type L-glutamate receptor and its ion channel was assayed using the electrically stimulated retractor unguis muscle of the locust (Schistocerca gregaria). Twitch amplitude was reduced from control levels: between $10^{-5}M$ and $10^{-4}M$ such that an approximately 50% reduction was obtained at $5 \times 10^{-5}M$.

EXAMPLE 13

N-(3-Hydroxycinnamoyl)-spermine

According to the General Procedure using 3-hydroxycinnamic acid (160 mg, 0.97 mMol), dicyclohexylcarbodiimide (226 mg, 1.10 mMol), and spermine (400 mg, 1.98 mMol) in dichloromethane (6 ml), activation during 2 h and coupling over 21 h. The product was eluted over silica gel with dichloromethane/methanol/0.880 ammonia solution (4:2:1). The desired amide was in fractions 15–22 and was homogeneous when monitored by tlc on silica ($CH_2Cl_2/MeOH/NH_4OH$, 4:2:1), $R_f=0.22$, (108 mg, 32%), lyophilisation gave 90 mg of a yellow viscous gum whose spectroscopic data include: $UV_{max}$ 213 ($e_{max}$ 3 500), 230sh and 375 ($e_{max}$ 3 800) nm; pmr (90 MHz, $^2H_2O$) 1.4–2.0 (m, 8H, $4 \times CH_2-CH_2$), 2.6–3.0 (m, 10H, $5 \times CH_2-N$), 3.35 (t, J=7, 2H, $CON^2H-CH_2-CH_2$), 6.4 (d, J=16, 1H, CH=CH—CO), 3.55 (s, 2H, Ar—CH$_2$—CO), 6.6–6.9 (m, 3H, 3×ArH 2,4,6), and 7.2–7.6 (m, 2H, ArH 5 and ArCH=CH)ppm; M+1 349 (FAB matrix m-nitrobenzyl alcohol) $C_{19}H_{32}N_4O_2$ requires M+ 348).

The potency of this monoacylated spermine as an antonist of the invertebrate L-quisqualate sub-type L-glutamate receptor and its ion channel was assayed using the electrically stimulated retractor unguis muscle of the locust (Schistocerca gregaria). Twitch amplitude was reduced from control levels at $9.2 \times 10^{-7}M$ by approximately 25%.

EXAMPLE 14

N-(3-Fluoro-4-hydroxyphenylacetyl)-spermine.

According to the General Procedure using 3-fluoro-4-hydroxyphenylacetic acid (85 mg, 0.50 mMol), dicyclohexylcarbodiimide (106 mg, 0.31 mMol), and spermine (512 mg, 2.53 mMol) in DME/DMF (4 ml, 3:1), activation during 2 h and coupling over 48 h. The product was eluted over silica gel with dichloromethane/methanol/0.880 ammonia solution (4:2:1). The desired amide was in fractions 12–19 and was homogeneous when monitored by tlc on silica ($CH_2Cl_2/MeOH/NH_4OH$, 4:2:1), $R_f=0.19$, (39 mg, 22%), lyophilisation gave 30 mg of a colourless, viscous oil whose spectroscopic data include: pmr (90 MHz, $^2H_2O$) 1.6–2.2 (m, 8H, $4 \times CH_2-CH_2$), 2.85–3.2 (m, 10H, $5 \times CH_2-N$), 3.4 (t, J=7, 2H, $CON^2H-CH_2-CH_2$), 3.6 (s, 2H, Ar—CH$_2$—CO), 6.8–7.1 (m, 2H, 2×ArH 5,6), and 7.1 (d, 3 J H—F=11, H, ArH 2)ppm.

The potency of this monoacylated spermine as an antagonist of the invertebrate L-quisqualate sub-type L-glutamate receptor and its ion channel was assayed using the electrically stimulated retractor unguis muscle of the locust (Schistocerca gregaria). Twitch amplitude was reduced from control levels between $10^{-4}M$ and $10^{-3}M$, such that an approximately 50% reduction was obtained at $5 \times 10^{-4}M$.

EXAMPLE 15

N-(2-Methoxyphenylacetyl)-spermine

According to the General Procedure using 2-methoxyphenylacetic acid (81 mg. 0.49 mMol), dicyclohexylcarbodiimide (53 mg, 0.26 mMol), and spermine (201 mg, 0.99 mMol) in DME (4 ml), activation during 2.5 h and coupling over 48 h. The produce was eluted over silica gel with the lower layer of dichloromethane/methanol/0.880 ammonia solution (2:1:1). The desired amide was in fractions 6–10 and was homogeneous when monitored by tlc on silica ($CH_2Cl_2/MeOH/NH_4OH$ lower layer, 2:1:1), $R_f=0.25$, (28 mg, 31%), lyophilisation gave 16 mg of a colourless, viscous oil whose spectroscopic data include: pmr (90 MHz, $^2H_2O$) 1.35–1.85 (m, 8H, $4 \times CH_2-CH_2$), 2.4–2.9 (m, 10H, $5 \times CH_2-N$), 3.25 (t, J=7, 2H, $CON^2H-CH_2-CH_2$), 3.5 (s, 2H, Ar—CH$_2$—CO), 3.83(s, 3H, OCH$_3$), 6.75–7.05 (m, 2H, 2×ArH 3,5), and 7.15–7.35 (m, 2H, 2×ArH 4,6)ppm.

The potency of this monoacylated spermine as a noncompetitive antagonist of the invertebrate L-quisqualate sub-type L-glutamate receptor and its ion channel was assayed using the electrically stimulated retractor unguis muscle of the locust (Schistocerca gregaria). Twitch amplitude was reduced from control (100%) levels between $1 \times 10^{-4}M$ and $1 \times 10^{-3}M$, such that an approximately 50% reduction was obtained at $5 \times 10^{-4}M$.

EXAMPLE 16

N-(4-Methoxyphenylacetyl)-spermine

According to the General Procedure using 4-methoxyphenylacetic acid (83 mg, 0.50 mMol), dicyclohexylcarbodiimide (56 mg, 0.27 mMol), and spermine (201 mg, 0.99 mMol) in DME (4 ml), activation during 2.5 h and coupling over 48 h. The product was eluted over silica gel with the lower layer of dichloromethane/methanol/0.880 ammonia solution (4:1:1). The desired amide was in fractions 16–25 and was homogeneous when monitored by tlc on silica (CH$_2$Cl$_2$/MeOH/NH$_4$OH lower layer, 4:1:1), R$_f$=0.07, (30 mg, 32%), lyophilisation gave 21 mg of a colourless, viscous oil whose spectroscopic data include: pmr (90 MHz, $^2$H$_2$O) 1.4–1.8 (m, 8H, 4×CH$_2$—CH$_2$), 2.4–2.9 (m, 10H, 5×CH$_2$—N), 3.3 (t, J=7, 2H, CON$^2$H—CH$_2$—CH$_2$), 3.5 (s, 2H, Ar—CH$_2$—CO), 3.83 (s, 3H, OCH$_3$), 6.8–6.95 (m, 2H, 2×ArH 3,5), and 7.1–7.3 (m, 2H, 2×ArH 2,6)ppm.

The potency of this monoacylated spermine as an antagonist of the invertebrate L-quisqualate sub-type L-glutamate receptor and its ion channel was assayed using the electrically stimulated retractor unguis muscle of the locust (*Schistocerca gregaria*). Twitch amplitude was reduced from control (100%) levels between 1×10$^{-4}$M and 1×10$^{-3}$M, such that an approximately 50% reduction was obtained at 5×10$^{-4}$M.

EXAMPLE 17

N-(2-Methoxyphenylacetyl)-N',N''-bis(3-aminopropyl)-1,3-propanediamine

According to the General Procedure using 2-methoxyphenylacetic acid (80 mg, 0.48 mMol), dicyclohexylcarbodiimide (106 mg, 0.51 mMol), and bis(3-aminopropyl)-1,3-propanediamine (452 mg, 2.40 mMol) in DME (4 ml, activation during 2 h and coupling over 48 h. The product was eluted over silica gel with the lower layer of dichloromethane/methanol/0.880 ammonia solution (2:1:1). The desired amide was in fractions 4–7 and was homogeneous when monitored by tlc on silica (CH$_2$Cl$_2$/MeOH/NH$_4$OH lower layer, 2:1:1), R$_f$=0.23, (55 mg, 34%) lyophilisation gave 54 mg of a colourless, viscous oil whose spectroscopic data include: pmr (90 MHz, C$^2$HCl$_3$) 0.9–1.4 (m, 4H, 4×NH), 1.3–2.0 (m, 6H, 3×CH$_2$—CH$_2$), 2.3–2.9 (m, 10H, 5×CH$_2$—N), 3.22 (app. q, J=7, 2H, CONH—CH$_2$—CH$_2$), 3.5 (s, 2H, Ar—CH$_2$—CO), 3.8(s, 3H, OCH$_3$), 6.35(br t, J=7, CONH—CH$_2$), 6.7–7.0 (m, 2H, 2×ArH 3,5), and 7.1–7.35 (m, 2H, 2×ArH 4,6)ppm.

The potency of this compound as an antagonist of the invertebrate L-quisqualate sub-type L-glutamate receptor and its ion channel was assayed using the electrically stimulated retractor unguis muscle of the locust (*Schistocerca gregaria*). Twitch amplitude was reduced from control (100%) levels between 1×10$^{-4}$M and 9×10$^{-3}$M, such that an approximately 50% reduction was obtained at 9×10$^{-4}$M.

EXAMPLE 18

N-(4-Methoxyphenylacetyl)-N',N''-bis(3-aminopropyl)-1,3-propanediamine

According to the General Procedure using 4-methoxyphenylacetic acid (80 mg, 0.48 mMol), dicyclohexylcarbodiimide (106 mg, 0.51 mMol), and bis(3-aminopropyl)-1,3-propanediamine (464 mg, 2.46 mMol) in DME (6 ml) activation during 2 h and coupling over 48 h. The product was eluted over silica gel with the lower layer of dichloromethane/methanol/0.880 ammonia solution (2:1:1). The desired amide was in fractions 4–8 and was homogeneous when monitored by tlc on silica (CH$_2$Cl$_2$/MeOH/NH$_4$OH lower layer, 2:1:1), R$_f$=0.30, (35 mg, 22%) lyophilisation gave 26 mg of a colourless, viscous oil whose spectroscopic data include: pmr (90 MHz, C$^2$HCl$_3$) 1.0–1.4 (m, 4H, 4×NH), 1.3–2.0 (m. 6H, 3×CH$_2$—CH$_2$), 2.2–2.9 (m, 10H, 5×CH$_2$—N, 3.25 (app. q, J=7, 2H, CONH—CH$_2$—CH$_2$), 3.42 (s, 2H, Ar—CH$_2$—CO), 3.76 (s, 3H, OCH$_3$), 6.63 (br t, J=7, CONH—CH$_2$), 6.8 (d, J=8, 2H, 2×ArH3,5), and 7.15 (d, J=8, 2H, 2×ArH 2,6)ppm.

The potency of this compound as an antagonist of the complex formed by the invertebrate L-quisqualate sub-type L-glutamate receptor and its ion channel was assayed using the electrically stimulated retractor unguis muscle of the locust (*Schistocerca gregaria*). Twitch amplitude was reduced from control (100%) levels between 1×10$^{-4}$M and 9×10$^{-3}$M, such that an approximately 50% reduction was obtained at 9×10$^{-4}$M.

EXAMPLE 19

N-(2-Hydroxyphenylacetyl)-N',N''-bis(3-aminopropyl)-1,3-propanediamine

According to the General Procedure using 2-hydroxyphenylacetic acid (160 mg, 1.05 mMol), dicyclohexylcarbodiimide (230 mg, 1.11 mMol), and bis(3-aminopropyl)-1,3-propanediamine (806 mg, 4.28 mMol) in DME (6 ml), activation during 4.5 h and coupling over 24 h. The product was eluted over silica gel with dichloromethane/- methanol/0.880 ammonia solution (4:2:1). The desired amide was in fractions 8–20 and was homogeneous when monitored by tlc on silica (CH$_2$Cl$_2$/MeOH/NH$_4$OH, 4:2:1), R$_f$=0.11, (235 mg, 69%), lyophilisation gave 188 mg of a colourless, viscous oil whose spectroscopic data include: pmr (90 MHz, C$^2$HCl$_3$) 1.4–1.8 (m, 6H, 3×CH$_2$—CH$_2$), 2.3–2.85 (m, 10H, 5×CH$_2$—N), 3.2 (t, J=7, 2H, CON$^2$H—CH$_2$—CH$_2$), 3.5 (s, 2H, Ar—CH$_2$—CO), 3.9 (br s, 6H, 5×NH and OH) 6.65–6.9 (m, 2H, 2×ArH 3,5), and 6.95–7.2 (m, 2H, 2×ArH 4,6)ppm.

The potency of this compound as an antagonist of the complex formed by the invertebrate L-quisqualate sub-type L-glutamate receptor and its ion channel was assayed using the electrically stimulated retractor unguis muscle of the locust (*Schistocerca gregaria*). Twitch amplitude was reduced from control (100%) levels between 1×10$^{-4}$M and 9×10$^{-3}$M, such that an approximately 50% reduction was obtained at 9×10$^{-4}$M.

EXAMPLE 20

N-(3-Hydroxyphenylacetyl)-N',N''-bis(3-aminopropyl)-1,3-propanediamine

According to the General Procedure using 3-hydroxyphenylacetic acid (150 mg, 0.98 mMol), dicyclohexylcarbodiimide (226 mg, 1.10 mMol), and bis(3-aminopropyl)-1,3-propanediamine (370 mg, 1.97 mMol) in dichloromethane (6 ml), activation during 2 h and coupling over 3 h. The product was eluted over silica gel with dichloromethane/methanol/0.880 ammonia solution (4:2:1). The desired amide was in fractions 13–21 and was homogeneous when monitored by tlc on silica (CH$_2$Cl$_2$/MeOH/NH$_4$OH, 4:2:1), R$_f$=0.27, (97 mg, 31%), lyophilisation gave 79 mg of a colourless, viscous oil whose spectroscopic data include: pmr (90 MHz, $^2$H$_2$O) 1.4–2.0 (m, 6H, 3×CH$_2$—CH$_2$), 2.3–2.9 (m, 10H, 5×CH$_2$—N), 3.25 (t, J=7, 2H, CON$^2$H—CH$_2$—CH$_2$), 3.5 (s, 2H, Ar—CH$_2$—CO), 6.55–6.75 (m, 3H, 3×ArH 2,4,6), and 7.05–7.3 (m, ArH 5)ppm.

The potency of this compound as an antagonist of the complex formed by the invertebrate L-quisqualate sub-type L-glutamate receptor and its ion channel was assayed using the electrically stimulated retractor unguis muscle of the locust (*Schistocerca gregaria*). Twitch amplitude was reduced from control (100%) levels at 1.04×10$^{-4}$M by approximately 60%.

EXAMPLE 21

N-(4-Hydroxyphenylacetyl)-N',N'''-bis(3-aminopropyl)-1,3-propanediamine

According to the General Procedure using 4-hydroxyphenylacetic acid (160 mg, 1.05 mMol), dicyclohexylcarbodiimide (231 mg, 1.12 mMol), and bis(3-aminopropyl)-1,3-propanediamine (806 mg, 4.28 mMol) in DME (6 ml), activation during 4.5 h and coupling over 48 h. The product was eluted over silica gel with dichloromethane/methanol/0.880 ammonia solution (4:2:1). The desired amide was in fractions 11–20 and was homogeneous when monitored by tlc on silica ($CH_2Cl_2$/MeOH/$NH_4OH$, 4:2:1), $R_f$=0.13, (88 mg 26%), lyophilisation gave 74 mg of a colorless gum whose spectroscopic data include: pmr (90 MHz, $^2H_2O$) (1.4–2.0 (m, 6H, 3×$CH_2$—$CH_2$), 2.4–2.9 (m, 10H, 5×$CH_2$—N), 3.18 (t, J=7, 2H, $CON^2H$—$CH_2$—$CH_2$), 3.4 (s, 2H, Ar—$CH_2$—CO), 6.68(d, J=8, 2H, 2×ArH 3,5), and 7.05(d, J=8, 2H, 2×ArH 2,6)ppm.

The potency of this compound as an antagonist of the complex formed by the invertebrate L-quisqualate subtype L-glutamate receptor and its ion channel was assayed using the electrically stimulated retractor unguis muscle of the locust (Schistocerca gregaria). Twitch amplitude was reduced from control (100%) levels between $1\times10^{-4}$M and $9\times10^{-3}$M, such that an approximately 50% reduction was obtained at $9\times10^{-4}$M, and on approximately 30% reduction at $1\times10^{-4}$M.

EVALUATION ON A MAMMALIAN NEURONAL PREPARATION

Method

Coronal slices of cerebral cortex were cut with a Vibratome from the brains of freshly killed Wistar rats. Wedges of tissue were cut from either side of the midline to include the cortex and corpus callosum. The wedges were mounted in a grease-gap apparatus such that the cortex protruded into one compartment and the corpus callosum into the other compartment of a two-compartment bath, (Harrison N. L. & Simmonds M. A. (1985). Br. J. Pharmacol 84: 381-391.). Each compartment could be separately perfused with Krebs bicarbonate medium pre-gassed with 95% $O_2$/5% $CO_2$ at room temperature. The volume of each compartment was 1.8 ml and the perfusion rate was 2 ml/min. The compartment containing the cortical part of the wedge was also gassed directly so that drugs could be injected into the bath with the perfusion pump stopped. This variant on the published method was adopted to minimise the amount of drug required. The potential difference between the two compartments was recorded continously via Ag/AgCl electrodes.

The polyamine compounds were tested for their ability to antagonise either the quizqualate receptor agonist (RS)-α-amino-3-hydroxy-5-methyl-4-isoxazolepropionic acid (AMPA) (Tocris Neuramin) or the NMDA receptor agonist N-methyl-D-aspartate (Sigma). The polyamine compounds were supplied as freeze-dried aliquots and, for each experiment, one of these was dissolved in sufficient distilled water to produce a 10 mM stock solution. To permit optimal responses to NMDA, $Mg^{2+}$ was omitted from the medium. Since this generally results in epileptiform discharges in the wedges, (Horne A. L., Harrison N. L., Turner J. P. and Simmonds M. A. (1986) Eur. J. Pharmacol 122: 231-238) tetrodotoxin (Sigma) was used to suppress such activity and was initially added to the bath to a concentration of 2.5 μM for 5 min. and thereafter was incorporated into the perfusion medium at a concentration of 0.1 μM.

The experimental protocol was to perfuse the tissue initially to obtain a steady baseline. The perfusion was then stopped and an aliquot of a 1 mM stock solution of either AMPA or NMDA was injected into the cortical compartment to give a concentration of 2.5 or 5 μM. Once the depolarisation response had reached its peak (usually within 3 min.), the perfusion was resumed to wash out the drug and return the potential to baseline. This procedure was repeated 3 or 4 times to achieve consistent responses. With the perfusion again stopped, the polyamine was injected into the cortical compartment to a concentration of 1, 10 or 100 μM, using stock solutions of 0.1, 1 or 10 mM, respectively. After 20 min, a dose of AMPA or NMDA was injected, as before, followed by the resumption of perfusion after the peak of the response. Repeated injections of AMPA or NMDA were made without further addition of the polyamine. In control experiments, no polyamine was injected.

COMPOUND OF EXAMPLE 3

The potency of this monoacylated spermine was tested as an antagonist of NMDA- and AMPA- induced response in a rat brain slice model. Electrophysiologically recorded depolarisation responses were reduced from control levels (% inhibition) at the following concentrations:

|            | AMPA | NMDA |
|------------|------|------|
| $10^{-6}$ M | 0%   | 29%  |
| $10^{-5}$ M | 22%  | 35%  |

We claim:

1. A compound of the formula:

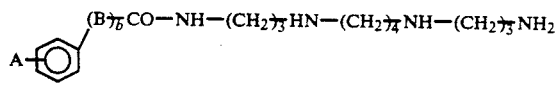

wherein:
A represents hydroxyl, O-alkyl or O-benzyl, B represents —$CH_2$— or —$CH_2CH_2$— and b is 0 or 1, and their pharmaceutically acceptable acid addition salts.

2. The compound of claim 1, wherein A represents a 4-position substituent.

3. The compound of claim 1, wherein A represents hydroxyl.

4. The compound of claim 2, wherein A represents hydroxyl.

5. A compound selected from the group consisting of N-(4-hydroxyphenylacetyl)-spermine, and N-(4-hydroxybenzoyl)-spermine and pharmaceutically acceptable acid addition salts thereof.

6. A method of treating a patient suffering from cerebral ischaemia, which comprises administering to such a patient a therapeutically effective amount of a compound claimed in claim 1.

7. The method of claim 6, wherein A represents a 4-position substituent.

8. The method of claim 6, wherein A represents hydroxyl.

9. The method of claim 7, wherein A represents hydroxyl.

10. The method of treating a patient suffering from cerebral ischaemia, which comprises administering to such a patient a therapeutically effective amount of a compound claimed in claim 5.

11. A pharmaceutical composition for the treatment of cerebral ischaemia, comprising a therapeutically effective amount of a compound claimed in claim 1 together with a pharmaceutically acceptable diluent or carrier.

12. The composition of claim 1, wherein A represents hydroxyl in the 4-position.

13. A pharmaceutical composition for the treatment of cerebral ischaemia, comprising a therapeutically effective amount of a compound claimed in claim 5 together with a pharmaceutically acceptable diluent or carrier.

14. The method of claim 6, wherein the patient is suffering from a stroke.

15. The method of claim 10, wherein the patient is suffering from a stroke.

* * * * *